United States Patent [19]
Fisher et al.

[11] Patent Number: 4,604,358
[45] Date of Patent: Aug. 5, 1986

[54] PREPARATION OF PASTEURIZED HUMAN PLASMINOGEN

[75] Inventors: Joseph D. Fisher, Chicago Heights; Chin C. Huang, Bourbonnais, both of Ill.

[73] Assignee: Armour Pharmaceutical Company, Tarrytown, N.Y.

[21] Appl. No.: 722,099

[22] Filed: Apr. 11, 1985

Related U.S. Application Data

[63] Continuation-in-part of Ser. No. 484,837, Apr. 14, 1983, abandoned.

[51] Int. Cl.$^4$ ........................... C12N 9/68; C12N 9/96
[52] U.S. Cl. ..................................... 435/217; 435/188
[58] Field of Search ............... 435/217, 216, 215, 212, 435/188

[56] References Cited

U.S. PATENT DOCUMENTS

| | | | |
|---|---|---|---|
| 3,066,079 | 11/1962 | Hagan et al. | 435/217 |
| 3,227,626 | 1/1966 | Baumgarten et al. | 435/217 |
| 3,340,156 | 9/1967 | Jensen et al. | 435/217 |
| 4,442,213 | 4/1984 | Heber et al. | 435/217 |

Primary Examiner—Lionel M. Shapiro

[57] ABSTRACT

This invention relates to a method for producing a plasminogen preparation which has been pasteurized to produce a hepatitis safe injectable plasminogen. The method comprises: adding to an aqueous solution of plasminogen the protective agent of methyl lysine ester, or ethyl lysine ester or a hydrochloride salt thereof which has antifibrinolytic acitivity to thereby attach the agent to plasminogen and form a modified plasminogen; and subjecting the resulting modified agent to a heat treatment of at least 60° C. for at least 10 hours. Further, the protective agent may be separated from the modified plasminogen by affinity chromatography.

7 Claims, No Drawings

PREPARATION OF PASTEURIZED HUMAN PLASMINOGEN

BACKGROUND OF THE INVENTION

This application is a continuation-in-part of co-pending application Ser. No. 484,837, filed Apr. 14, 1983, now abandoned.

FIELD OF THE INVENTION

This invention relates to a method for producing a plasminogen preparation which has been pasteurized to produce a hepatitis free plasminogen. More particularly, this invention relates to a method of pasteurizing plasminogen in the presence of a plasminogen protecting agent which has antifibrinolytic activity and thereby to produce a hepatitis free injectable plasminogen.

DESCRIPTION OF THE PRIOR ART

Plasminogen, also known as profibrinolysin, serum tryptase, and plasma trypsinogen, is the inactive plasma protein precursor of the proteolytic enzyme, plasmin. Plasminogen may be converted to plasmin by combining it in a known manner with an activator, such as streptokinase, staphylokinase and chloroform.

Plasmin is used for the treatment of acute thromboembolic disorders as it enzymatically lysis blood clots. For this purpose the plasmin may be injected directly into the thrombus itself or it may be given intravenously.

A variety of methods can be used to isolate and purify plasminogen. For example, it can be isolated from human plasma by the procedure of Cohn employing cold ethanol fractionation (procedure described in "The Proteins," Vol. 2, 1954, pages 663–754, edited by Neurath and Baily, published by Academic Press). Plasminogen is found most abundantly in Cohn's Fraction III. It can be further purified by various procedures such as by the subfractionation procedure of Cohn which yields Fraction III-3 or other preparations containing a similarly high concentration of plasminogen.

Plasminogen so obtained and purified may be contaminated with hepatitis virus because of the possibility that the virus was present in the blood of the donor. The presence of the virus cannot be detected with known certainty by any method used heretofore. For obtaining a hepatitis free product the plasminogen or the plasmin derived from it must be sterilized to destroy the virus.

It is known that heat treatment at 60° C. or higher for a period of 10 hours or more will inactivate hepatitis virus in various plasma fractions. Most experience has been gained with the sterilization of albumin solutions. Albumin solutions have been pasteurized for 10 hours at 60° C. at pH 6.9±0.5 and acetyl-troptophane and sodium caprylate have been employed as stabilizers. Attempts have been made to sterilize plasminogen preparation by similar methods but it was found that the enzymatic activity of plasminogen was completely destroyed under these conditions. It was found, however, that plasminogen solution could be heated for 10 hours at 60° C. if the pH was adjusted to 3.5. Under these conditions, only a fraction of the total activity could be recovered. Obviously, treatment of plasminogen at a low unphysiological pH is undesirable, and furthermore the losses on heating are great and at times reproducible yield are not obtained.

Plasminogen has also been heat sterilized in the presence of lysine, and also in the presence of combinations of aprotinin with glycine, $\alpha$- or $\beta$-alanine, lysine, arginin, histidine, hydroxyproline, proline, glutamine and mono- or oligosaccharide or sugar alcohol. While hepatitis safe plasminogen has been prepared by the use of these agents, total activity recovered varied widely and often found to be very low.

SUMMARY OF THE INVENTION

It has now been discovered that if a heat treatment at 60° C. or higher for a period of 10 hours or more is applied to plasminogen to which certain protective agents have been attached, the so protected plasminogen will survive and can be recovered in high yields while at the same time the hepitatis virus or particles thereof are inactivated.

When added to plasminogen these protective agents become attached to the plasminogen in such a way as to modify the plasminogen and enable it to survive the heat treatment of 60° C. or higher for 10 hours or more. The protective agents which we found especially suitable for the purpose of the present invention are ethyl lysine ester, methyl lysine ester and their mono- and di-hydrochloride salts.

Briefly defined, the pasteurization process is accomplished by heating at 60° C. or higher for 10 hours or longer an aqueous solution comprising: 1 to 1.7 mg/ml plasminogen in the presence of 0.15 to 0.2M methyl lysine ester, ethyl lysine ester, or a mono- or di-hydrochloride salt thereof.

It was found that best result is obtained when the ratio of plasminogen to the protective agent concentration is about 1 to $1 \times 10^4$. More specifically, the optimum plasminogen concentration in the pasteurization solution is about 1.5 mg/ml and that of the stabilizer is about 4.5 mg/ml.

DETAILED DESCRIPTION OF THE INVENTION

To carry out the process, we start with plasminogen obtained from the Cohn plasma fraction III which has been purified preferably by affinity chromatography using lysine Sepharose.

A quantity of the purified plasminogen material as obtained from human blood may be dissolved in a buffer solution. To this solution we add the protective agent. The pH is adjusted to about neutral, such as between pH 6 and pH 8. The resulting solution may be placed in a water bath equipped with means for controlling the temperature, and heated to at least 60° C. ($\pm 0.5$° C.) and held at this temperature for at least 10 hours.

Since there may be a possibility that the protecting agent has in itself, some physiological effect, we sought to find some method by which the protective agent could be removed. We discovered that by subjecting the pasteurized plasminogen (containing the protective agent) to affinity chromatography, the protective agent may be removed. In this procedure, we may add the pasteurized plasminogen to a lysine-Sephadex column and selectively remove plasminogen from the medium. The plasminogen may be desorbed and so freed from the protective agent. Alternatively, the plasminogen may be separated from the protecting agent by subjecting it to a column containing Sephadex. In this way we may separate the protective agent from plasminogen by virtue of the differences in molecular weight. The resulting plasminogen, free of the protecting agent, may be filtered and lyophilized for storage.

In our process the protecting agent forms an attachment to the plasminogen which modifies the plasminogen and allows it to survive the rugged heat treatment which is required for pasteurization. It is not clear at this time where in the molecular structure this attachment takes place or if true chemical bonds are involved in the modification, but it is clear that the attachment modifies the plasminogen so as to enable it to survive the heat treatment necessary for pasteurization.

The heat treatment of the protected plasminogen at a temperature of at least 60° C. for at least 10 hours effectively destroys the hepatitis viral activity if any be contained therein, and the pasteurized plasminogen is safe for injection intravenously into humans in the treatment of blood clots.

To further demonstrate the practice of our improved processes we include the following specific examples:

EXAMPLE 1

1550 ml of highly purified human plasminogen was obtained from the human plasma fraction III (Cohn fraction III ppt) by lysine Sepharose affinity chromatography. The plasminogen solution, containing 4.15 gm/ml of protein was dissolved in buffer solution containing 0.1M lysine, 0.05 NaCl, 0.01M $Na_2HPO_4$ and 0.01 citric acid. To this solution 2738 ml of additional solution containing 192.9 gms L-lysine ethyl ester was added; pH was adjusted to 7.4. The total volume was 4288 ml. Plasminogen activity was 7.65 CLN units/ml; protein concentration was 1.5 gms/ml. The plasminogen solution with the protecting agent was placed in a water bath and held at 60° C. for 10 hours to pasteurize. After pasteurization the plasminogen activity was 7.06 CLN units/ml. This is translated to a recovery of plasminogen of 7.06/7.65, which is 93%.

EXAMPLE 2

200 ml of pasteurized plasminogen prepared according to the procedure of Example 1 having 12.52 mg/ml was applied to a Sephadex G-50 column (5.0×5.8 cm), was equilibrated with pH 7.4 buffer solution containing 0.1M lysine, 0.05M NaCl, 0.01M $Na_2HPO_4$ and 0.01M citric acid. The same buffer solution was used to elute plasminogen molecules which was eluted at void volume and yielded 300 ml with 8.71 CLN units/ml. The total activity applied to the column was equal to 2504 CLN units and the total yield activity was 2613/2504 or 104%. Although it is obvious that this cannot be precisely correct, it is within the range allowed for error.

EXAMPLE 3

A purified human plasminogen solution was prepared by affinity chromatography, as in Example 1.

This plasminogen solution was stored at −70° C. for one month, then thawed at 4° C. Protein concentration was 2.42 mg/ml. Plasminogen activity was 13.7 CLN units/ml. Total volume was 2450 ml. The protecting agent was lysine ethyl ester. 180 gms of this agent was dissolved in 1550 ml of buffer solution containing 0.1M lysine, 0.05M NaCl, 0.01M $Na_2HPO_4$, 0.01M citric acid, then added to the plasminogen solution to make a total volume of 4000 ml, and protein concentration became 1.48 mg/ml. Plasminogen activity before pasteurization was 8.68 CLN units/ml which translates to a recovery of 7.2/8.68 or 83%.

The plasminogen solution was desalted on a Sephadex G-50 column followed by sterile filtration, vialing and lyophilization for long term storage.

EXAMPLE 4

This example shows the effect of plasminogen concentration, stabilizer concentration (methyl lysine ester, MLE; ethyl lysine ester, ELE) and the ratio of stabilizer to plasminogen on the physical properties, clearness, precipitation, and the yield of plasminogen activity. The process described in Example 1 was used in this study. Pasteurization conditions were: 60° C.; sample shaken in water bath for 11 hours. The result is shown in Table I.

TABLE I

Protection of Plasminogen Activity by Stabilizer During Pasteurization

| Conc. Plasminogen | Stabilizer ELE or MLE | Ratio Stabilizer/ Plasminogen | PPT After 11 Hrs. 60° C. | CLN U./ml. Plasminogen Activity Before Past. | After Past. | % Recovery |
|---|---|---|---|---|---|---|
| 5 μM (0.2 mg/ml) | ELE 50 mM | 1 × $10^4$ | − | 1.30 | 1.39 | 106 |
| 10 μM (0.4 mg/ml) | ELE 100 mM | 1 × $10^4$ | − | 2.70 | 2.58 | 95.6 |
| 20 μM (0.8 mg/ml) | ELE 200 mM | 1 × $10^4$ | ++ | 5.24 | 4.14 | 79.6 |
| 25 μM (1.0 mg/ml) | ELE 50 mM | 2 × $10^3$ | + | 8.04 | 5.88 | 73.1 |
| 25 μM (1.0 mg/ml) | ELE 25 mM | 1 × $10^3$ | ++ | 7.58 | 5.88 | 77.8 |
| 5 μM (0.2 mg/ml) | MLE 50 mM | 1 × $10^4$ | − | 1.77 | 1.05 | 59.0 |
| 10 μM (0.4 mg/ml) | MLE 100 mM | 1 × $10^4$ | − | 3.01 | 2.13 | 70.7 |
| 20 μM (0.8 mg/ml) | MLE 200 mM | 1 × $10^4$ | ++ | 5.34 | 2.88 | 54.0 |
| 25 μM (1.0 mg/ml) | MLE 50 mM | 2 × $10^3$ | + | 9.08 | 6.04 | 66.5 |
| 25 μM (1.0 mg/ml) | MLE 25 mM | 1 × $10^3$ | ++ | 9.68 | 5.88 | 61.1 |

+, ++: Indicates amount of precipitates in this and subsequent Tables
−: Indicates lack of precipitates in this and subsequent Tables

EXAMPLE 5

This example shows the use of ethyl lysine ester dihydrochloride as the protecting agent. The process of Example 1 was used. Pasteurization was accomplished at the temperature of 60° C. for 10 hours. The result is shown in Table II.

TABLE II

Protection of Plasminogen by Ethyl Lysine Ester Dihydrochloride During Pasteurization at 60° C. for 10 Hrs.

| Batch Size | Plasminogen Concentration mg/ml | ELE Concentration mg/ml | Ratio Stabilizer/ Plasminogen | PPT After 10 Hrs. 60° C. | CLN U./ml. Plasminogen Activity Before | CLN U./ml. Plasminogen Activity After | % Recovery |
|---|---|---|---|---|---|---|---|
| 4280 ml. | 1.5 (1.8 $\mu$M) | 45 (0.182 M) | $1 \times 10^4$ | + | 7.65 | 7.06 | 93 |
| 100 ml. | 1.5 (1.8 $\mu$M) | 45 (0.182 M) | $1 \times 10^4$ | + | 4.78 | 4.44 | 93 |
| 4 ml. | 1.71 (2.05 $\mu$M) | 49.4 (0.199 M) | $0.97 \times 10^4$ | ++ | 7.20 | 6.64 | 92 |
| 1000 ml. | 1.03 (1.24 $\mu$M) | 37.0 (0.150 M) | $1.2 \times 10^4$ | + | 5.08 | 4.82 | 94 |
| 4 ml. | 1.3 (1.55 $\mu$M) | 37.1 (0.150 M) | $1 \times 10^4$ | + | 4.08 | 5.04 | 123 |
| 4 ml. | 1.5 (1.8 $\mu$M) | 43.3 (0.180 M) | $1 \times 10^4$ | + | 6.36 | 6.24 | 98 |

EXAMPLE 6 (Comparative Example)

The procedure of Example 1 was used in this study to determine whether other protective agents, instead of methyl lysine ester, ethyl lysine ester and their hydrochloride salts, could be used to protect plasminogen during the pasteurization process. The agents used were lysine and Σ-amino caproic acid. The result is shown in Table III.

TABLE III

Protection of Plasminogen Activity by Lysine and Σ-amino Caproic Acid During Pasteurization

| Conc. Plasminogen | Stabilizer | Ratio Stabilizer/ Plasminogen | PPT After 11 Hrs. 60° C. | CLN U./ml. Plasminogen Activity Before Past. | CLN U./ml. Plasminogen Activity After Past. | % Recovery |
|---|---|---|---|---|---|---|
| | Lysine | | | | | |
| 5 $\mu$M (0.2 mg/ml) | 50 mM | $1 \times 10^4$ | − | 1.82 | 0.495 | 27.2 |
| 10 $\mu$M (0.4 mg/ml) | 100 mM | $1 \times 10^4$ | − | 3.15 | 1.27 | 40.3 |
| 20 $\mu$M (0.8 mg/ml) | 200 mM | $1 \times 10^4$ | − | 6.60 | 2.53 | 38.3 |
| 25 $\mu$M (1.0 mg/ml) | 50 mM | $2 \times 10^3$ | + | 8.60 | 1.52 | 17.7 |
| 25 $\mu$M (1.0 mg/ml) | 25 mM | $1 \times 10^3$ | ++ | 7.28 | 1.12 | 15.4 |
| | Σ-ACA | | | | | |
| 5 $\mu$M (0.2 mg/ml) | 50 mM | $1 \times 10^4$ | − | 0.81 | 0.255 | 31.5 |
| 10 $\mu$M (0.4 mg/ml) | 100 mM | $1 \times 10^4$ | − | 2.72 | 0.34 | 12.5 |
| 20 $\mu$M (0.8 mg/ml) | 200 mM | $1 \times 10^4$ | − | 6.52 | 0.58 | 8.9 |
| 25 $\mu$M (1.0 mg/ml) | 50 mM | $2 \times 10^3$ | − | 8.20 | 1.98 | 24.1 |
| 25 $\mu$M (1.0 mg/ml) | 25 mM | $1 \times 10^3$ | − | 6.56 | 1.84 | 28.4 |

It is apparent from Table III that recovery is very low as compared to the result shown in Tables I and II.

While we have described in detail certain embodiments of the invention it is apparent that other embodiments may be practiced and that many changes may be made, all within the spirit of the invention and the scope of the appended claims.

What is claimed is:

1. A method for pasteurizing plasminogen comprising the steps of:
    treating an aqueous solution of unpasteurized plasminogen by adding to said solution a protecting agent selected from the group consisting of methyl lysine ester, ethyl lysine ester or a hydrochloride salt thereof to thereby attach said agent to plasminogen and form modified plasminogen; and
    subjecting the resulting modified plasminogen to a heat treatment of at least 60° C. for at least 10 hours.

2. The method of claim 1 further comprising the step of separating said protective agent from said modified pasteurized plasminogen by affinity chromatography.

3. A method as set forth in claim 2 in which said separation includes applying said modified plasminogen to a column containing Sephadex G-50, and eluting the column to recover plasminogen free of said protecting agent.

4. The method of claim 1 wherein the concentration ratio of said plasminogen to said protecting agent is about 1 to $1 \times 10^4$.

5. A method for pasteurizing plasminogen comprising the steps of:
    treating an aqueous solution of about 1 to 1.7 mg/ml unpasteurized plasminogen by adding to said solution about 0.15 to 0.2M of a protecting agent selected from the group consisting of methyl lysine ester, ethyl lysine ester or a hydrochloride salt thereof to thereby attach said agent to plasminogen and form modified plasminogen; and
    subjecting the resulting modified plasminogen to a heat treatment of at least 60° C. for at least 10 hours.

6. The method of claim 5 further comprising the step of separating said protective agent from said modified pasteurized plasminogen by affinity chromatography.

7. A method as set forth in claim 6 in which said separation includes applying said modified plasminogen to a column containing Sephadex G-50, and eluting the column to recover plasminogen free of said protecting agent.

* * * * *